United States Patent
Knowland et al.

(10) Patent No.: US 6,869,596 B1
(45) Date of Patent: Mar. 22, 2005

(54) ULTRAVIOLET LIGHT SCREENING COMPOSITIONS

(75) Inventors: John Sebastian Knowland, Oxford (GB); Peter James Dobson, Oxford (GB); Gareth Wakefield, Oxford (GB)

(73) Assignee: ISIS Innovation Limited, Summertown (GB)

( * ) Notice: Subject to any disclaimer, the term of this patent is extended or adjusted under 35 U.S.C. 154(b) by 0 days.

(21) Appl. No.: 09/701,213

(22) PCT Filed: May 27, 1999

(86) PCT No.: PCT/GB99/01685

§ 371 (c)(1),
(2), (4) Date: Apr. 16, 2002

(87) PCT Pub. No.: WO99/60994

PCT Pub. Date: Dec. 2, 1999

(30) Foreign Application Priority Data

May 27, 1998 (GB) ............................. 9811377

(51) Int. Cl.[7] ............................. A61K 7/42; C09C 1/04; C01G 45/12; C01G 45/02; C01G 23/047
(52) U.S. Cl. ...................... 424/59; 424/401; 106/286.4; 106/286.6; 106/287.19; 106/425; 106/430; 423/274; 423/598; 423/599; 423/605; 423/607; 423/610; 423/622
(58) Field of Search ................ 424/401, 59; 106/286.4, 106/286.6, 287.19, 425, 430, 1.29; 423/274, 598, 599, 605, 607, 610, 622

(56) References Cited

U.S. PATENT DOCUMENTS

| | | | |
|---|---|---|---|
| 2,028,980 A | | 1/1936 | Korinth ........................ 134/78 |
| 3,884,871 A | * | 5/1975 | Herman et al. ........... 260/42.14 |
| 5,298,067 A | * | 3/1994 | Valet et al. .................. 106/506 |
| 5,441,726 A | | 8/1995 | Mitchnick et al. ............ 424/59 |
| 5,451,252 A | | 9/1995 | Elfenthal et al. ........... 106/436 |
| 5,754,001 A | * | 5/1998 | Ohno et al. .................. 313/497 |
| 5,776,239 A | | 7/1998 | Bruno ......................... 106/437 |
| 5,800,824 A | | 9/1998 | Pfrommer et al. .......... 424/401 |
| 5,876,688 A | * | 3/1999 | Laundon ..................... 423/622 |
| 5,973,175 A | | 10/1999 | Bruno .......................... 556/56 |
| 6,090,200 A | * | 7/2000 | Gray et al. ................... 117/68 |
| 6,180,029 B1 | * | 1/2001 | Hampden-Smith et al. ...... 252/301.4 R |
| 6,235,270 B1 | * | 5/2001 | Ishii et al. ..................... 424/59 |

FOREIGN PATENT DOCUMENTS

| | | |
|---|---|---|
| DE | 2545243 A1 | 4/1977 |
| EP | A-0 579 062 | 1/1994 |
| EP | A-0 768 078 | 4/1997 |
| EP | A-0 768 277 | 4/1997 |
| GB | 1 386 549 * | 3/1975 |
| JP | 9188517 A | 1/1996 |
| JP | 11279019 | 12/1999 |
| WO | WO B-0 482 444 | 5/1994 |
| WO | WO 97/15526 | 5/1997 |
| WO | WO 99/46204 | 9/1999 |

OTHER PUBLICATIONS

Choi et al., "J. Phys. Chem., The Role of Metal Ion Dopants in Quantum–Sized $TiO_2$: Correlation between Photoreactivity And Charge Carrier Recombination Dynamics", (1994), 98, 13669–13679.

* cited by examiner

Primary Examiner—Michael G. Hartley
Assistant Examiner—Marina Lamm
(74) Attorney, Agent, or Firm—Wolf, Greenfield & Sacks, P.C.

(57) ABSTRACT

A UV screening composition comprising particles which are capable of absorbing UV light so that electrons and positively charged holes are formed within the particles, characterised in that the particles are adapted to minimise migration to the surface of the particles of the electrons and/or the positively charged holes when said particles are exposed to UV light in an aqueous environment.

10 Claims, 6 Drawing Sheets

ULTRAVIOLET LIGHT SCREENING COMPOSITIONS

BACKGROUND OF THE INVENTION

The present invention relates to UV screening compositions, methods for their preparation and their use. The invention in particular relates to, for example, compositions comprising particulate oxides, their preparation and their use as, for example, paints, plastics, coatings, pigments, dyes and compositions for topical application, in particular, for example, sunscreens.

The effects associated with exposure to sunlight are well known. For example, painted surfaces may become discoloured and exposure of skin to UVA and UVB light may result in, for example, sunburn, premature ageing and skin cancer.

Commercial sunscreens generally contain components which are able to reflect and/or absorb UV light. These components include, for example, inorganic oxides such as zinc oxide and titanium dioxide.

Titanium dioxide in sunscreens is generally formulated as "micronised" or "ultrafine" (20–50 nm) particles (so-called microreflectors) because they scatter light according to Rayleigh's Law, whereby the intensity of scattered light is inversely proportional to the fourth power of the wavelength. Consequently, they scatter UVB light (with a wavelength of from 290 to 320 nm) and UVA light (with a wavelength of from 320 to 400 nm) more than the longer, visible wavelengths, preventing sunburn whilst remaining invisible on the skin.

However, titanium dioxide also absorbs UV light efficiently, catalysing the formation of superoxide and hydroxyl radicals which may initiate oxidations. The crystalline forms of $TiO_2$, anatase and rutile, are semiconductors with band gap energies of about 3.23 and 3.06 eV respectively, corresponding to light of about 385 nm and 400 nm (1 eV corresponds to 8066 $cm^{-1}$).

An incident photon is absorbed by titanium dioxide if its energy is greater than the semiconductor band gap Eg shown in FIG. 1. As a result an electron from the valence band (vb) is promoted into the conduction band (cb) (transition [1]). If the energy of the incident photon is less than Eg it will not be absorbed as this would require that the electron be promoted to within the band gap and this energy state is forbidden. Once promoted, the electron relaxes to the bottom of the conduction band (transition [2]) with the excess energy being emitted as heat to the crystal lattice.

When the electron is promoted it leaves behind a hole which acts as a positive particle in the valence band. Both the electron and the hole are then free to migrate around the titanium dioxide particle. The electron and hole may recombine emitting a photon of energy equal to the band gap energy. However, the lifetime of the electron/hole pair is quite long due to the specific nature of the electronic band structure. Thus there is sufficient time (ca. $10^{-11}$s) for the electron and hole to migrate to the surface and react with absorbed species.

In aqueous environments, the electrons react with oxygen, and the holes with hydroxyl ions or water, forming superoxide and hydroxyl radicals:

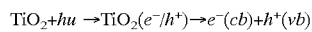

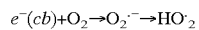

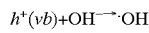

This has been studied extensively in connection with total oxidation of environmental pollutants, especially with anatase, the more active form [A. Sclafani et al., J. Phys. Chem., (1996), 100, 13655–13661].

It has been proposed that such photo-oxidations may explain the ability of illuminated titanium dioxide to attack biological molecules. Sunscreen titanium dioxide particles are often coated with compounds such as alumina, silica and zirconia which form hydrated oxides which can capture hydroxyl radicals and may therefore reduce surface reactions. However, some $TiO_2/Al_2O_3$ and $TiO_2/SiO_2$ preparations exhibit enhanced activity [C. Anderson et al., J. Phys. Chem., (1997), 101, 2611–2616].

As titanium dioxide may enter human cells, the ability of illuminated titanium dioxide to cause DNA damage has also recently been a matter of investigation. It has been shown that particulate titanium dioxide as extracted from sunscreens and pure zinc oxide will, when exposed to illumination by a solar simulator, give rise to DNA damage both in vitro and in human cells [R. Dunford et al, FEBS Lett., (1997), 418, 87–90].

The present invention provides UV screening compositions which address the problems described above and are less liable to produce DNA damage on illumination than conventional sunscreen compositions.

SUMMARY OF THE INVENTION

The present invention accordingly provides UV screening compositions comprising particles which are capable of absorbing UV light, especially UV light having a wavelength below 390 nm, so that electrons and positively charged holes are formed within the particles, characterised in that the particles are adapted to minimise migration to the surface of the particles of the electrons and/or the positively charged holes when said particles are exposed to UV light in an aqueous environment. It is believed that under these circumstances the production of hydroxyl radicals is substantially reduced. Thus the production of hydroxyl radicals may be substantially prevented.

The minimisation of migration to the surface of the particles of the electrons and/or the positively charged holes may be tested by, for example, looking for a reduction in the number of strand breaks inflicted on DNA by light in the presence of particles or UV screening compositions according to the present invention, as compared with the number of strand breaks observed in DNA on treatment with particles used in conventional sunscreen compositions and light, or light alone.

The compositions according to the present invention may find application as paints, plastics, coatings, pigments, dyes and are particularly favoured for use in compositions for topical application, especially, for example, sunscreens.

The average primary particle size of the particles is generally from about 1 to 200 nm, for example about 50 to 150 nm, preferably from about 1 to 100 nm, more preferably from about 1 to 50 nm and most preferably from about 20 to 50 nm. For example, in sunscreens the particle size is preferably chosen to avoid colouration of the final product. For this purpose particles of about 50 nm or less may be preferred especially, for example, particles of about 3 to 20 nm, preferably about 3 to 10 nm, more preferably about 3 to 5 nm.

Where particles are substantially spherical then particle size will be taken to represent the diameter. However, the invention also encompasses particles which are non-spherical and in such cases the particle size refers to the largest dimension.

In a first embodiment the present invention provides UV screening compositions comprising particles which contain luminescence trap sites and/or killer sites. By luminescence trap sites and killer sites will be understood foreign ions designed to trap the electrons and positively charged holes and therefore inhibit migration.

These particles may be, for example, reduced zinc oxide particles, especially reduced zinc oxide particles of from about 100 to 200 nm in size or smaller, for example, from about 20 to 50 nm.

Such reduced zinc oxide particles may be readily obtained by heating zinc oxide particles which absorb UV light, especially UV light having a wavelength below 390 nm, and reemit in the UV in a reducing atmosphere to obtain reduced zinc oxide particles which absorb UV light, especially UV light having a wavelength below 390 nm, and reemit in the green, preferably at about 500 nm. It will be understood that the reduced zinc oxide particles will contain reduced zinc oxide consistent with minimising migration to the surface of the particles of electrons and/or positively charged holes such that when said particles are exposed to UV light in an aqueous environment the production of hydroxyl radicals is substantially reduced as discussed above.

The zinc oxide is preferably heated in an atmosphere of about 10% hydrogen and about 90nitrogen by volume, e.g. at about 800 ° C. and for about 20 minutes.

It is believed that the reduced zinc oxide particles possess an excess of $Zn^{2+}$ ions within the absorbing core. These are localised states and as such may exist within the band gap. Transitions [1] and [2] may occur as shown in FIG. 1. However, the electron and hole may then relax to the excess $Zn^{2+}$ states (transition [3]) as shown in FIG. 2. Thus the electrons and holes may be trapped so that they cannot migrate to the surface of the particles and react with absorbed species. The electrons and holes may then recombine at the $Zn^{2+}$ states (transition [4]) accompanied by the release of a photon with an energy equivalent to the difference in the energy levels.

Alternatively, particles of the present invention may comprise a host lattice incorporating a second component to provide luminescence trap sites and/or killer sites. The host lattice may be preferably selected from oxides, especially, for example, $TiO_2$ and ZnO, or for example, phosphates, titanates, silicates, aluminates, oxysilicates, tungstates and molybdenates. The second component may, for example, be selected according to criteria such as ionic size. Second components suitable for 5 use according to the present invention may, for example, be selected from nickel, iron, chromium, copper, tin, aluminium, lead, silver, zirconium, manganese, zinc, cobalt and gallium ions. Preferably the second component is selected from iron, chromium, manganese and gallium ions in the 3+state. Preferred particles according to the present invention comprise a titanium dioxide host lattice doped with manganese ions in the 3+state.

The optimum amount of the second component in the host lattice may be determined by routine experimentation. It will be appreciated that the amount of the second component may depend on the use of the UV screening composition. For example, in UV screening compositions for topical application, it may be desirable for the amount of the second component in the host lattice to be low so that the particles are not coloured. In the case of titanium dioxide doped with manganese ions in the 3+state, 0.5% manganese in the titanium dioxide host lattice has been shown to be effective in reducing the rate of DNA damage inflicted by simulated sunlight. However, amounts as low as 0.1% or less, for example 0.05%, or as high as 1% or above, for example 5% or 10%, may also be used.

The dopant ions may be incorporated into the host lattice by a baking technique typically at from 600° C. to 1000° C. Thus, for example, these particles may be obtained in a known manner by combining a host lattice with a second component to provide luminescence trap sites and/or killer sites.

It is envisaged that the mechanism of de-excitation for these particles is as described above for the reduced zinc particles.

In a further embodiment the present invention provides UV screening compositions comprising particles which comprise a population of coated nanoparticles of a metal oxide. The metal oxide is preferably titanium dioxide. The coating is typically a wide band gap material and is preferably a surfactant selected from trioctylphosphine oxide [TOPO] and sodium hexametaphosphate [$(NaPO_3)_6$].

The nanoparticles are generally from 1 to 10 nm in size and possibly from 1 to 5 nm in size.

It has been found that the nanoparticles may be obtained by dissolving a titanium salt, preferably titanium (IV) chloride, in an alcohol. The alcohol is 5 generally selected from methanol, ethanol, propanol and butanol. Preferably the alcohol is methanol or propanol. The dehydrating properties of the alcohol may help to inhibit formation of the hydroxide phase. A surfactant is added to bind to the titanium ions and form a surface layer. Typically the ratio of titanium ions to surfactant is 1:1.

The pH of the solution is then monitored while a solution of sodium hydroxide in alcohol, preferably a 1M solution in methanol, is added dropwise until the oxide nanoparticles precipitate. The alcohol is evaporated so that the oxide particles flocculate. The particles may be washed to remove excess surfactant and the remaining alcohol is then evaporated to leave the titanium dioxide nanoparticles as a powder. Preparation of the nanoparticles is generally carried out in an inert atmosphere, preferably an atmosphere of nitrogen or argon. A population of the nanoparticles may then be combined to form the larger particles of the present invention.

On absorption of UV light the electrons and holes produced may be confined to a specific nanoparticle within the particles of the present invention thus minimising migration of the electrons and/or the holes to the surface of the particles. The nanoparticles may also be beneficial in that the rate of recombination of the electrons and holes may be increased. The electrons and holes may recombine with the emission of a photon of energy equal to the band gap as shown in FIG. 3.

The particles of the present invention may have an inorganic or organic coating. For example, the particles may be coated with oxides of elements such as aluminium, zirconium or silicon. The particles of metal oxide may also be coated with one or more organic materials such as polyols, amines, alkanolamines, polymeric organic silicon compounds, for example, $RSi[OSi(Me)_2xOR^1]_3$ where R is $C_1$-$C_{10}$ alkyl, $R^1$ is methyl or ethyl and x is an integer of from 4 to 12, hydrophilic polymers such as polyacrylamide, polyacrylic acid, carboxymethyl cellulose and xanthan gum or surfactants such as, for example, TOPO.

As indicated above, compositions of the invention may be used in a wide range of applications where UV screening is desired, but are particularly preferred for topical application. The compositions for topical application may be, for example, cosmetic compositions, compositions for protecting the hair, or preferably sunscreens. Compositions of the present invention may be employed as any conventional formulation providing protection from UV light.

In compositions for topical application, the metal oxides are preferably present at a concentration of about 0.5 to 10 % by weight, preferably about 3 to 8 % by weight and more preferably about 5 to 7% by weight. Such compositions may comprise one or more of the compositions of the present invention.

The compositions for topical application may be in the form of lotions, e.g. thickened lotions, gels, vesicular dispersions, creams, milks, powders, solid sticks and may be optionally packaged as aerosols and provided in the form of foams or sprays.

The compositions may contain, for example, fatty substances, organic solvents, silicones, thickeners, demulcents, other UVA, UVB or broad-band sunscreen agents, antifoaming agents, moisturizing agents, perfumes, preservatives, surface-active agents, fillers, sequesterants, anionic, cationic, nonionic or amphoteric polymers or mixtures thereof, propellants, alkalizing or acidifying agents, colorants and metal oxide pigments with a particle size of from 100 nm to 20000 nm such as iron oxides.

The organic solvents may be selected from lower alcohols and polyols such as ethanol, isopropanol, propylene glycol, glycerin and sorbitol.

The fatty substances may consist of an oil or wax or mixture thereof, fatty acids, fatty acid esters, fatty alcohols, vaseline, paraffin, lanolin, hydrogenated lanolin or acetylated lanolin.

The oils may be selected from animal, vegetable, mineral or synthetic oils and especially hydrogenated palm oil, hydrogenated castor oil, vaseline oil, paraffin oil. Purcellin oil, silicone oil and isoparaffin.

The waxes may be selected from animal, fossil, vegetable, mineral or synthetic waxes. Such waxes include beeswax, Carnauba, Candelilla, sugar cane or Japan waxes, ozokerites, Montan wax, microcrystalline waxes, paraffins or silicone waxes and resins.

The fatty acid esters are, for example, isopropyl myristate, isopropyl adipate, isopropyl palmitate, octyl palmitate, $C_{12}$-$C_{15}$ fatty alcohol benzoates ("FINSOLV TN" from FINETEX), oxypropylenated myristic alcohol containing 3 moles of propylene oxide ("WITCONOL APM" from WITCO), capric and caprylic acid triglycerides ("MIGLYOL 812" from HULS).

The compositions may also contain thickeners which may be selected from cross-linked or non cross-linked acrylic acid polymers, and particularly polyacrylic acids which are cross-linked using a polyfunctional agent, such as the products sold under the name "CARBOPOL" by the company GOODRICH, cellulose, derivatives such as methylcellulose, hydroxymethylcellulose, hydroxypropyl methylcellulose, sodium salts of carboxymethyl cellulose, or mixtures of cetylstearyl alcohol and oxyethylenated cetylstearyl alcohol containing 33 moles of ethylene oxide.

When the compositions of the present invention are sunscreens they may be in a form of suspensions or dispersions in solvents or fatty substances or as emulsions such as creams or milks, in the form of ointments, gels, solid sticks or aerosol foams. The emulsions may further contain anionic, nonionic, cationic or amphoteric surface-active agents. They may also be provided in the form of vesicular dispersions of ionic or nonionic amphiphilic lipids prepared according to known processes.

In another aspect the present invention provides a method for preparing the compositions of the present invention which comprises associating the particles described above with a carrier.

In another aspect the present invention provides particles comprising a host lattice incorporating a second component to provide luminescence trap sites and/or killer sites.

In a further aspect the present invention provides particles which comprise a population of coated nanoparticles of a metal oxide.

DESCRIPTION OF THE PREFERRED EMBODIMENTS

Figure 1:
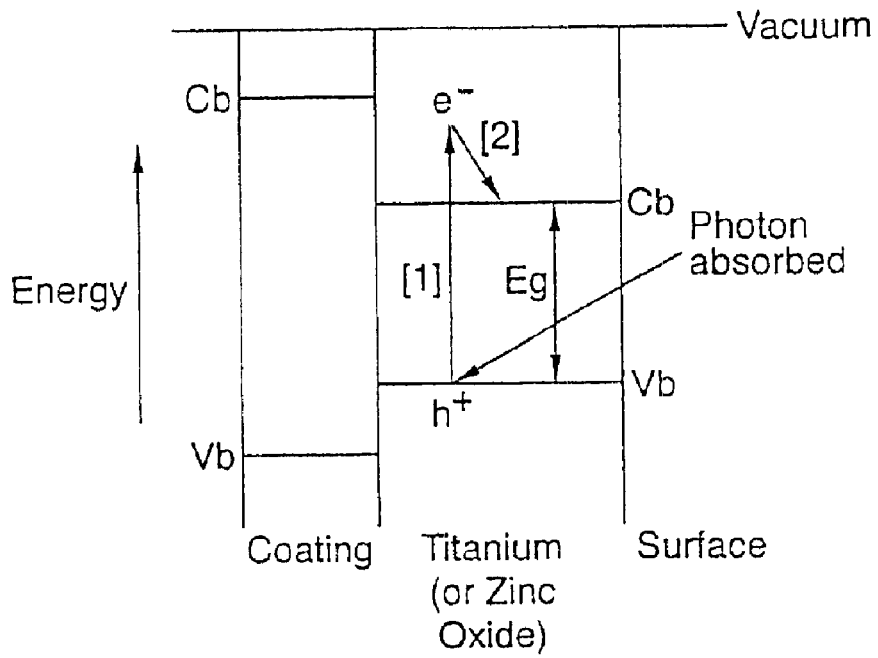
FIG. 1 shows the absorption of a photon of UV light by titanium dioxide as found in conventional sunscreens.
Figure 2:
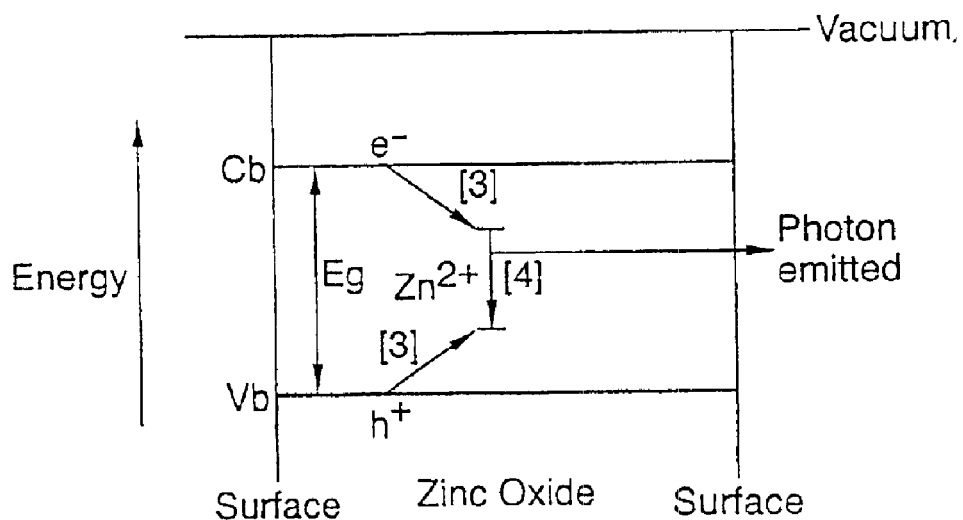
FIG. 2 shows the absorption of a photon of UV light by reduced zinc oxide particles.
Figure 3:
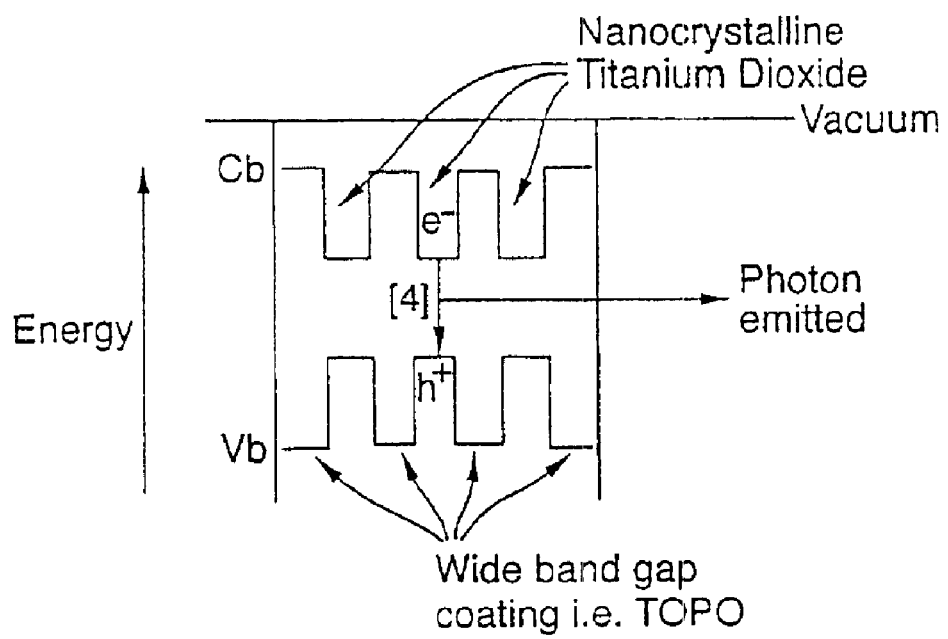
FIG. 3 shows the absorption of UV light by particles of the present invention which comprise at least two coated nanoparticles of titanium dioxide.

The Examples which follow farther illustrate the present invention with reference to the figures.

COMPARATIVE EXAMPLE

Chemical Oxidation by Titanium Dioxide Preparations $TiO_2$ samples were extracted from over-the-counter sunscreens by washing with organic solvents (methyl cyanide, acetone, chloroform), and their anatase and rutile contents were determined by X-ray diffraction methods. Anatase and rutile standards were obtained from Tioxide Group Services Ltd., Grimsby, UK. $TiO_2$ concentrations were assayed according to the method of Codell [M. Codell, (1959), Analytical Chemistry of Titanium Metal and Compounds, Interscience, New York] using standards made from pure $TiO_2$ (Aldrich); the molar extinction coefficient for the complex was assayed as 827 $M^{-1}$ at 404 nm. The photo-oxidation degradation of phenol by illuminated $TiO_2$ was monitored using high pressure liquid chromatography [N. Serpone et al., (1996), J. Photochem. Photobiol. A: Chem 94, 191–203] to measure its disappearance, employing isocratic procedures at ambient temperature on a Waters 501 liquid chromatograph equipped with a Waters 441 detector set at 214 nm and a HP 3396A recorder. The column was a Waters $\mu$BONDAPAK C-18 reverse phase and the mobile phase was a 50:50 mixture of methanol (BDH Omnisolv grade) and distilled/deionised water. Each sunscreen $TiO_2$ was illuminated at 0.05% by weight in 58 ml of phenol (200$\mu$M in air-equilibrated aqueous media, Ph 5.5; retention time of phenol in the HPLC chromatogram was 5 min) using a 1000-W Hg/Xe lamp and a 365 nm (±10 nm) interference filter, giving a light flux between 310 and 400 nm of ca. 32 mW $cm^{-2}$.

Appropriate aliquots (1ml) of the irradiated dispersion were taken at various intervals and filtered through a 0.1 $\mu$m membrane to remove the $TiO_2$ prior to analysis.

Illumination of DNA in Vitro The solar simulator [J. Knowland et al., (1993), FEBS Lett. 324, 309–313] consists of a 250-W ozone-free lamp, a WG 320 filter and a quartz lens, resulting in an estimated fluence between 300 and 400 nm of 12 W $m^{-2}$ DNA was the plasmid pBluescript II $SK^+$ (Stratagene) prepared and analyzed on agarose gels according to [T. Maniatis et al., (1982), Molecular Cloning: A Laboratory Manual, Cold Spring Harbor Laboratory, Cold Spring Harbor, N.Y.]. Relaxed standards were made by depurinating plasmid in 25 mM sodium acetate pH 4.8 at 70° C. for 20 min followed by cleaving with exonuclease III at 37° C. [N. Serpone, (1997), Photochem. Photobiol. A. 104, 1] in 50 mM Tris-HCl, 5 mM $CaCl_2$ (the $Ca^{2+}$ inhibits exonuclease but not cleavage at apurinic sites), 0.2 mM DTT, pH 8; linear standards by cutting with EcoRI. The authentic $TiO_2$ standards (confirmed by X-ray diffraction to be 100% anatase or 100% rutile) were suspended in water at 2% w/v; ZnO (Aldrich, <1 $\mu$m) at 0.4% w/v. 25 $\mu$l of each were added to 25 $\mu$l of plasmid (2–3 $\mu$g of DNA) in 100 mM sodium phosphate pH 7.4 and illuminated as droplets (50 $\mu$l) on siliconised microscope slides placed on a brass block embedded in ice. A sunscreen containing only $TiO_2$ (7% w/v) was vortexed with water and centrifuged. The white pellet was washed 3 times with a mixture of chloroform and methanol (1:1), then with methanol alone, and dried. The powder was suspended in water at 2%, but most quickly settled out, leaving a cloudy supernatant with a $TiO_2$ content assayed at 0.025% w/v. This was mixed with an equal volume of plasmid DNA in buffer and illuminated. Direct strand breaks were assayed from the conversion of super-coiled plasmid to the relaxed form.

Illumination of DNA in Vivo (Comet Assays)

Human cells (MRC-5 fibroblasts) were illuminated on ice with or without sunscreen $TiO_2$ (0.0125% w/v). The lens was omitted, giving an intensity similar to that found under the stratum corneum [Knowland, J. et al., (1993), FEBS Lett. 324, 309–313]. Samples were taken at increasing times, kept on ice, and analysed at the same time. For analysis, cells were embedded in low-melting agarose, lysed with 1% Triton X-100, subjected to alkaline gel electrophoresis and stained with ethidium bromide [P. W. Doetsch and R. P. Cunningham, (1990), Mutat. Res. 13, 3285–3304], and classified according to the five main standard classes [V. J. McKelvey-Martin et al., (1993), Mutat. Res. 228, 47–63].

Oxidation of organic materials by hydroxyl radicals from illuminated TiO can be examined conveniently by following the oxidation of a test molecule such as phenol [N. Serpone et al., (1996), J. Photochem. Photobiol. A: Chem. 94, 191–203]. The table below compares the oxidative degradation of phenol by $TiO_2$ samples from 10 different sunscreens with oxidation catalysed by pure rutile and pure anatase.

TABLE

Photodegradation of phenol by $TiO_2$ samples

| Sample | Anatase/rutile ratio (%) | Phenol photodegradation (mmol $h^{-1}$) | Relative rate |
|---|---|---|---|
| SN1[a] | 50/50 | 0.008 ± 0.016 | 1.0 |
| SN2 | 0/100 | 0.023 ± 0.008 | 2.8 |
| SN3 | 0/100 | 0.043 ± 0.010 | 5.2 |
| SN4 | 54/46 | 0.043 ± 0.007 | 5.2 |
| SN5 | 0/100 | 0.086 ± 0.015 | 10.4 |
| SN6 | 100/0 | 0.146 ± 0.014 | 17.6 |
| SN7[a] | 0/100 | 0.189 ± 0.008 | 22.7 |
| SN8 | 100/0 | 0.44 ± 0.11 | 53.3 |
| SN9 | 63/37 | 1.11 ± 0.03 | 134 |

TABLE-continued

Photodegradation of phenol by TiO$_2$ samples

| Sample | Anatase/rutile ratio (%) | Phenol photodegradation (mmol h$^{-1}$) | Relative rate |
| --- | --- | --- | --- |
| SN10[b] | 0/100 | 1.50 ± 0.04 | 180 |
| Pure rutile | 0/100 | 3.55 ± 0.12 | 427 |
| Pure anatase | 100/0 | 31.6 ± 0.8 | 3803 |

SN1–10 are over-the-counter sunscreens.
[a]Also contains Al(OH)$_3$.
[b]Also contains 1.95% ZnO.

All TiO$_2$ samples oxidise phenol, but activity does not depend solely on crystal type. The most active sample, SN10, also contains ZnO.

Figure 4:
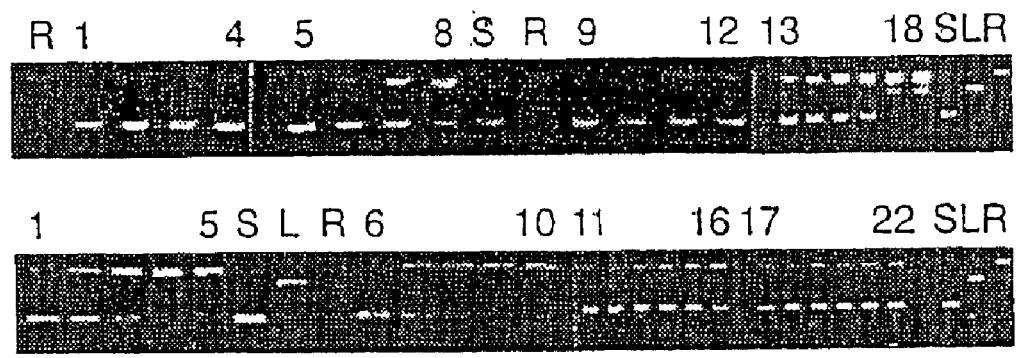
FIG. 4 shows relaxation of plasmids caused by illuminated $TiO_2$ and ZnO and suppression by DMSO and mannitol. In both panels, S, L and R show the migration of supercoiled, linear and relaxed plasmid. The top panel shows the plasmid relaxation found after illumination with sunlight alone for 0, 20, 40 and 60 min (lanes 1–4) and with 1% anatase (lanes 5–8) or 1% rutile (lanes 9–12 ) $TiO_2$ for the same times. Lanes 13–18 shows illumination with $TiO_2$ from sunscreen SN8 for 0, 5, 10, 20, 40 and 60 min. The results are typical of those found with various samples. The bottom panel shows illumination with 0.2% ZnO for 0, 10, 20, 40 and 60 min before (lanes 1–5) or after (lanes 6–10) adding DMSO; and with 0.0125% sunscreen $TiO_2$ for 0, 5, 10, 20, 40 and 60 min after adding 200 mM DMSO (lanes 11–16) or 340 mM mannitol (lanes 1–22).

Hydroxyl radicals inflict direct strand breaks on DNA, and to test for such damage supercoiled plasmids were illuminated with simulated sunlight and TiO$_2$. FIG. 4 shows that plasmids were converted first to the relaxed form and ultimately to the linear form, demonstrating strand breakage. Sunlight alone had very little effect, while anatase is more active than rutile, consistent with photochemical comparisons (Table 1 and [A. Sclafani and J. M. Herrmann, (1996), J. Phys. Chem. 100, 13655–13661]. TiO$_2$ extracted from a sunscreen is also photo-active, and so is pure ZnO. The sunscreen illuminations contain much less TiO$_2$ than the anatase and rutile ones, suggesting that the sunscreen variety is especially active. Damage was suppressed by the quenchers dimethylsuphoxide (DMSO) and mannitol, suggesting that it is indeed caused by hydroxyl radicals.

Figure 5:
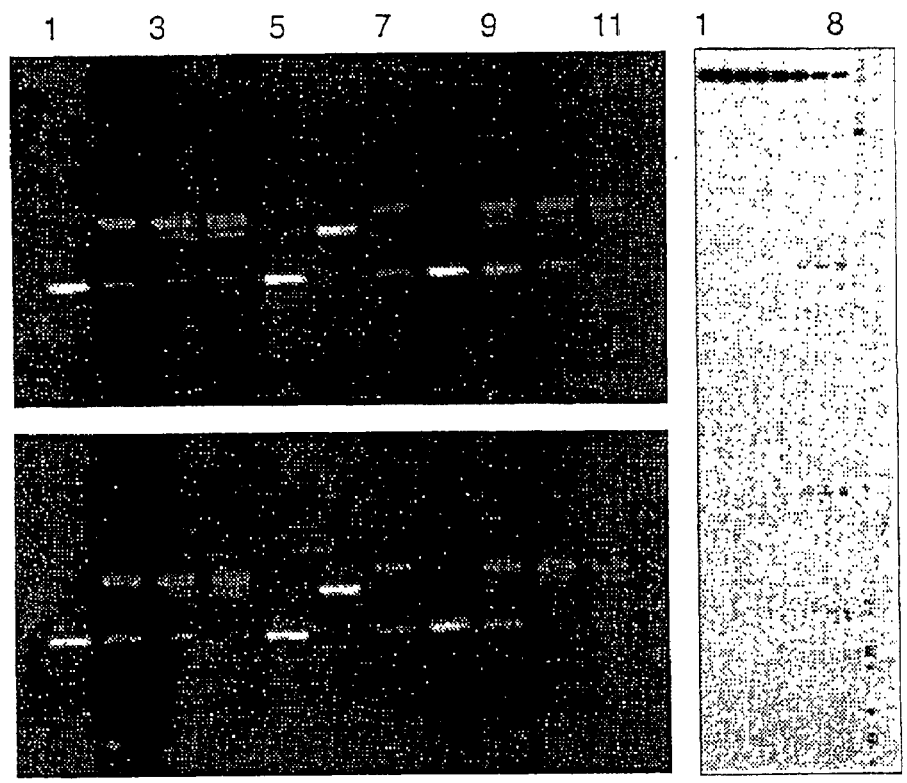
FIG. 5 shows the effect of catalase on damage inflicted by illuminated TiO2 and location of lesions in DNA. The top panel shows plasmid DNA which was illuminated (see FIG. 4) with sunscreen $TiO_2$ alone for 0, 20, 40 and 60 min (lanes 1–4) and for the same times (lanes 8–11) after adding 2.5 units/$\mu$l of catalase (0.1mg/ml of protein). Lanes 5–7 show supercoiled, linear and relaxed plasmid. The bottom panel shows illumination with sunscreen $TiO_2$ as above after adding boiled catalase (lanes 1–4) or 0.1 mg/ml of bovine serum albumin (lanes 8–11). The right panel shows a 426 bp fragment of double-stranded DNA labelled at one 5'-end which was illuminated in 0.0125% sunscreen $TiO_2$ and samples which were analyzed on a sequencing gel. Lanes 1–4 show illumination for 0, 20, 40 and 60 min. Lanes 5–8 show illumination for the same times followed by treatment with N,N'-dimethylethylenediamine for 30 min at 90° C. before analysis. This reagent displaces many damaged residues from DNA and then cleaves the sugar-phosphate chain, leaving homogeneous, phosphorylated termini with consistent mobility, thus clarifying the spectrum of lesions generated. Lanes 9–10 show G and A dideoxy sequencing standards.

FIG. 5 shows (top panel) that damage was very slightly suppressed by catalase, but also (bottom panel) that heat-inactivated catalase and bovine serum albumin have similar effects, suggesting that this limited quenching was due to the protein present rather than to catalase activity. Superoxide dismutase did not suppress the damage either (data not shown). It appears therefore that the strand breaks are not caused by superoxide (O$_2^-$), an active oxygen species formed by reaction between e$^{31}$ (cb) and O$_2$, and do not depend upon the intermediate formation of hydrogen peroxide by reaction between 2·OH radicals. Rather, they appear to be due to direct attack by hydroxyl radicals, which is consistent with indications that hydroxyl radicals formed on TiO$_2$ remain on the surface of the particles. By cleaving end-labelled DNA, other lesions were revealed (right panel), principally at some, but not all, guanine residues. Evidently, DNA damage is not confined to strand breaks.

Comet assays (FIG. 6) show that DNA in human cells is also damaged by illuminated TiO$_2$, consistent with endocytosis of TiO$_2$. Suppression by DMSO again implies that the damage is caused by hydroxyl radicals. These assays detect direct strand breaks and alkali-labile sites, and reveal the damage attribution to TiO$_2$.

Thus, illuminated sunscreen TiO$_2$ and ZnO can cause oxidative damage to DNA in vitro and in cultured human fibroblasts. This has important implications for use of conventional compositions for topical applications. Autoradiographic studies using $^{65}$ZnO have suggested that it passes through rat and rabbit skin, probably through hair follicles, although the chemical form of the $^{65}$Zn detected under the skin (and hence of the form that crosses the skin) is not clear. Some reports have raised the possibility that ZnO and pigmentary TiO$_2$ pass through human skin, and a recent one suggests that micronised TiO$_2$ in sunscreens does too [M.-H. Tan et al, Austalas. J. Dermatol, (1996), 37, 185–187]. It is therefore important to characterise the fate and photochemical behaviour of sunscreens, which certainly prevent sunburn, because they are also intended to reduce skin cancers, which have increased rapidly recently.

EXAMPLE 1
Preparation of Reduced Zinc Oxide Particles

The zinc oxide used was supplied by Aldrich. It has a particle size of 100–200 nm and absorbs in the UV below 390 nm and reemits at 390 nm. It was heated in an atmosphere of 10% hydrogen to 90% nitrogen by volume at 800° C. for 20 minutes. Reduced zinc oxide was obtained and was found to absorb in the UV and reemit in the green at 500 nm.

EXAMPLE 2
Comparison of Strand Breaks Inflicted on DNA by Sunlight in the Presence of Either Normal or Reduced Zinc Oxide.

Figure 7:
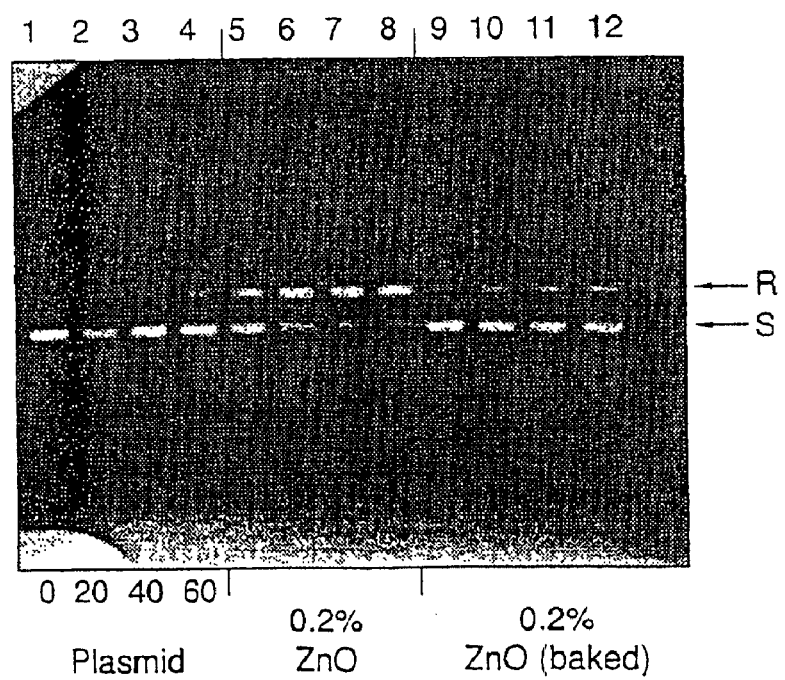
FIG. 7 shows a comparison of strand breaks inflicted on DNA by sunlight in the presence of either normal zinc oxide or the zinc oxide of the present invention. Lanes 1–4 show illumination with light alone for 0, 20, 40, 60 minutes; lanes 5–8 show illumination with normal ZnO (Aldrich) for 0, 10, 20, 40 and 60 minutes; and lanes 9–12 show illumination with reduced ZnO for 0, 20, 40 and 60 minutes.
Figure 6A:
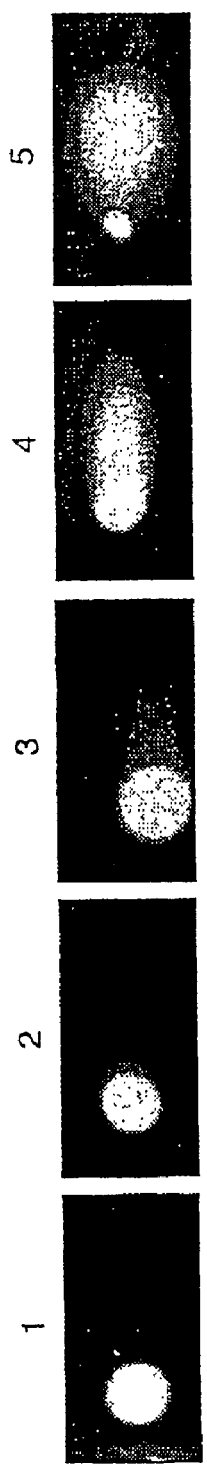
FIG. 6 shows the damage inflicted on human cells revealed by comet assays. Row A shows comets obtained using X-rays from a Gavitron RX30 source. The dose rate was 8.9 Gy min$^{-1}$ and cells were exposed on ice for 0, 15, 30 and 60 s, giving comets falling into the five main standard classes shown. 1, class 0; 2, class 1; 3, class II; 4, class III; 5, class IV. Rows B and C show examples of comets obtained using simulated sunlight, MRC-5 fibroblasts and sunscreen $TiO_2$ (0.0125%). For each exposure, 100 cells were scored, and comets were classified by comparison with the standards (row A). Row B shows no treatment (1); sunlight alone for 20, 40 and 60 min (2–4); and effect of $TiO_2$ in the dark for 60 min (5). Row C shows sunlight with $TiO_2$ for 0, 20, 40 and 60 min (1–4); and for 60 min with $TiO_2$ and 200 mM DMSO (5). The charts summarise results from five independent experiments. D shows that sunlight alone inflicts few strand breaks and/or alkali-labile sites and E that inclusion of $TiO_2$ catalyses this damage.
Figure 6B:
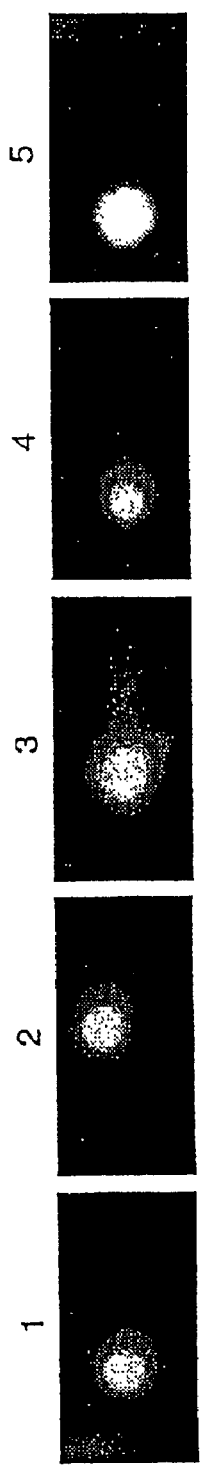
Figure 6C:
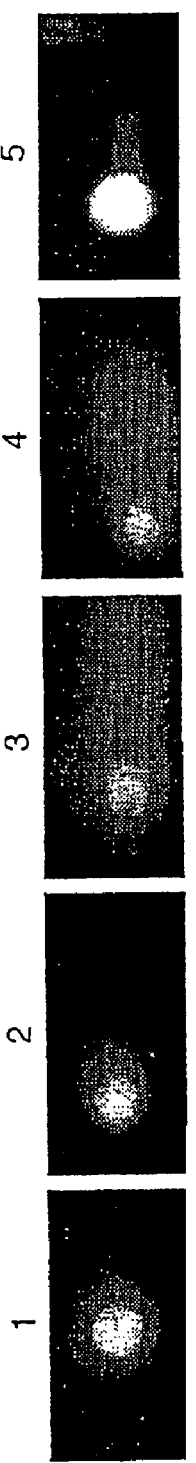
Figure 6D:
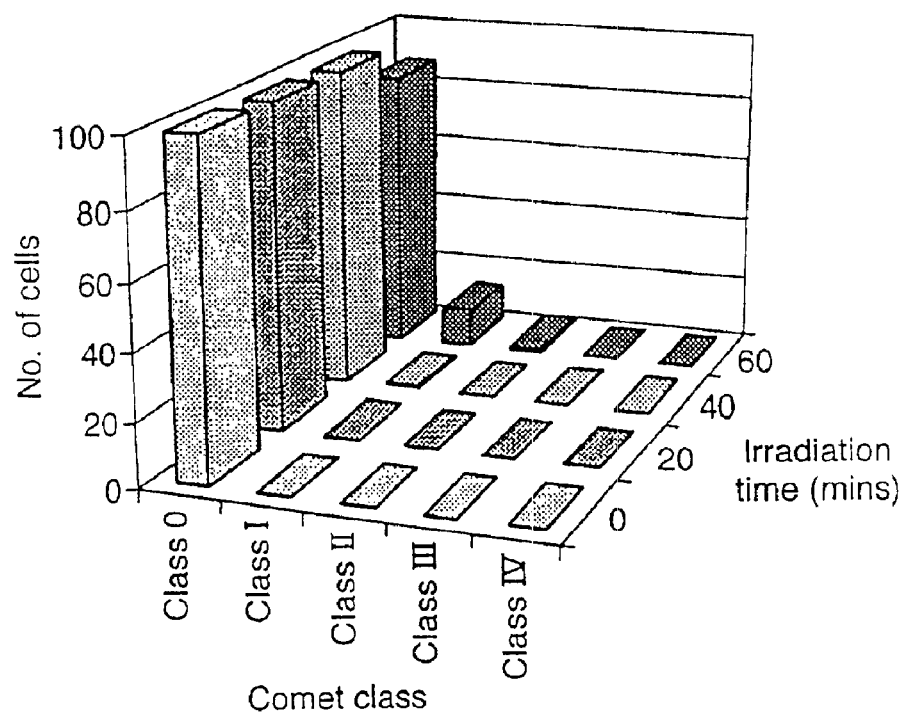
Figure 6E:
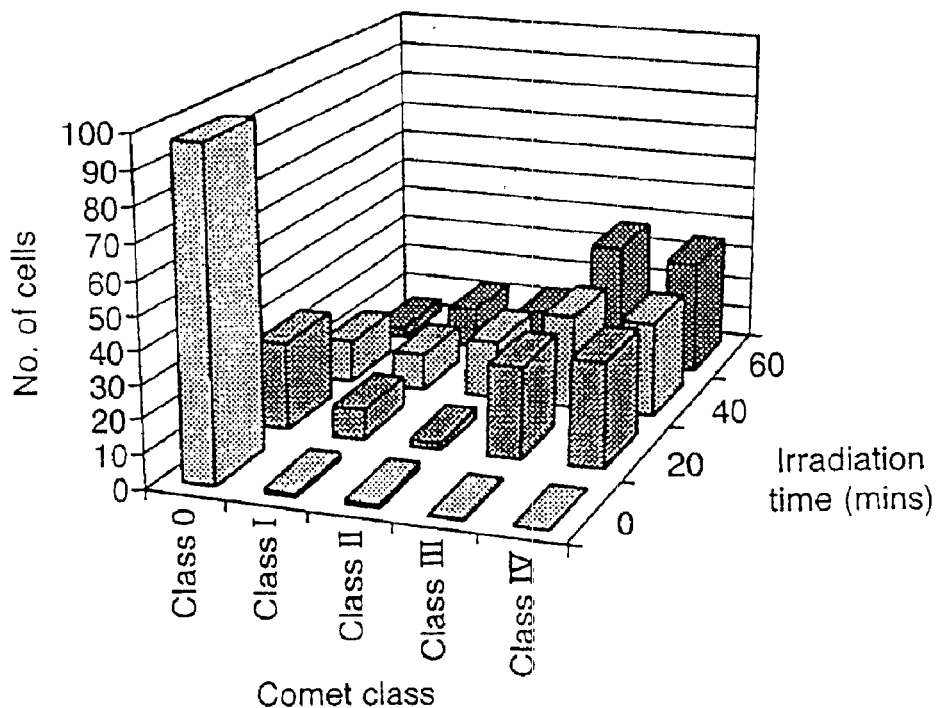

The DNA used was the plasmid pBluescript II SK$^+$ (Stratagene) prepared and analyzed on agarose gels according to T. Maniatis et al. [Molecular Cloning: A Laboratory Manual. Cold Spring Harbor Laboratory, Cold Spring Harbor, N.Y. (1982)]. It was illuminated in vitro using a solar simulator [J. Knowland et al, FEBS Lett., 324 (1993) 309–313] consisting of a 250 watt ozone-free lamp, a WG 320 filter and a quartz lens, resulting in an estimated fluence between 300 and 400 nm or 12 Watts.m$^{-2}$. Zinc oxide samples were suspended in water at 0.4% w/v. 25 μl of each suspension was added to 25 μl of plasmid (2–3 μg of DNA) in 100 mM sodium phosphate pH 7.4 and illuminated as droplets (50μl) on siliconised microscope slides placed on a brass block embedded in ice. Direct strand breaks were assayed from the conversion of supercoiled plasmid to the relaxed form, marked S and R on FIG. 7.

It was observed that illuminated reduced ZnO particles are very much less liable to produce DNA damage than conventional ZnO particles.

EXAMPLE 3
Preparation of Manganese Doped Titanium Dioxide.

Titanium dioxide (25 g) and manganese (II) nitrate (0.8 g) were mixed in deionized water (100 ml). The resulting mixture was ultrasonicated for 10 minutes and then boiled dry. The material produced was fired at 700° C. for 3 hours to give 1% manganese doped titanium dioxide. Titanium dioxide particles with differing dopant levels were prepared in an analogous manner by varying the amount of manganese (II) nitrate.

It is believed that manganese 3+ions (oxidised from manganese 2+during boiling) are incorporated into the surface of the titanium dioxide host lattice.

EXAMPLE 4
Assessment of the Effect of Varying the Percentage of Manganese in a Titanium Dioxide Host Lattice.

The ability of different manganese doped titanium dioxide particles to damage DNA was measured using the plasma nicking assays described in the Comparative Example above.

Figure 8:
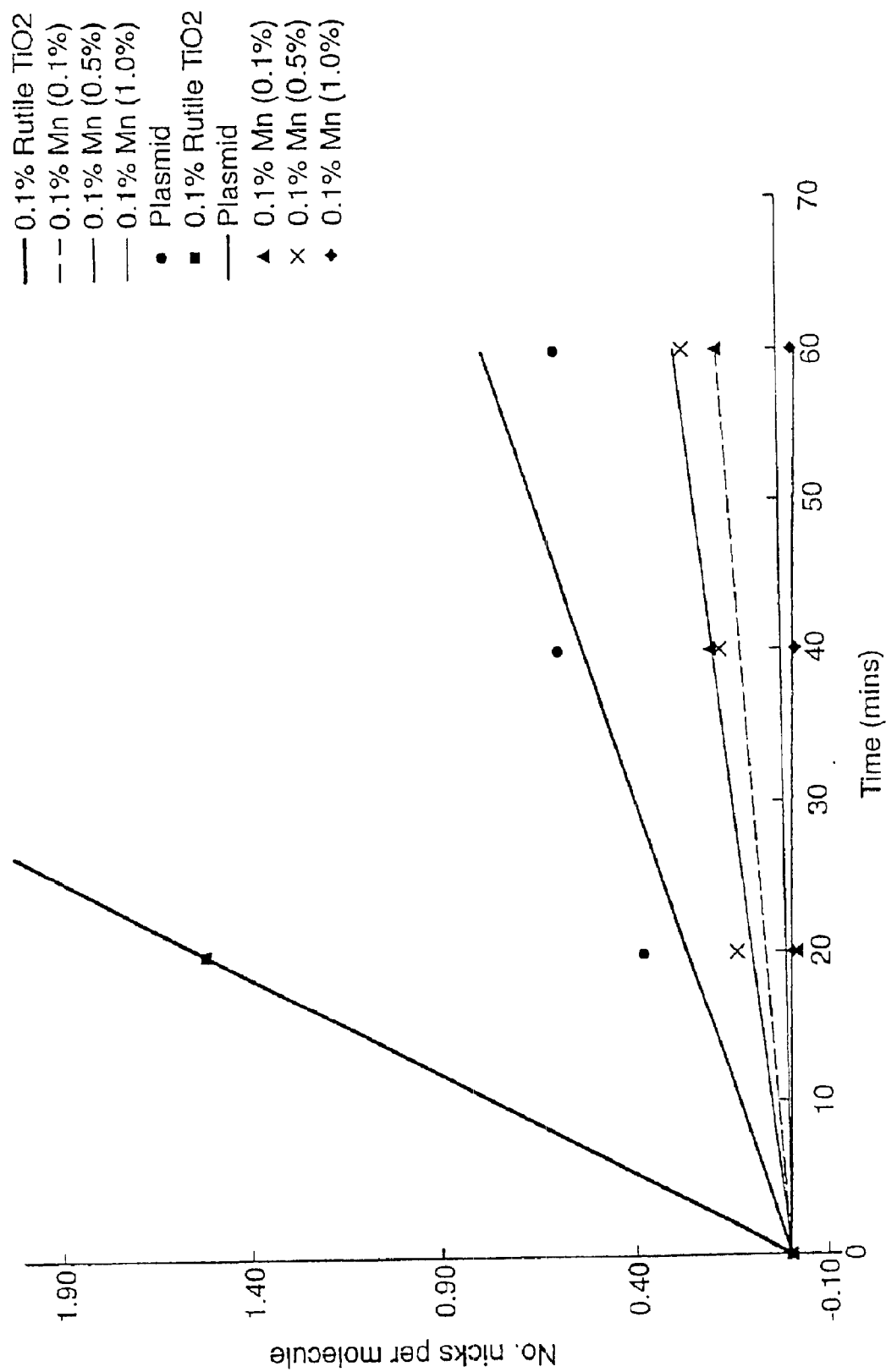
FIG. 8 shows the degradation of DNA irradiated in the presence of manganese doped titanium dioxide. The Figure shows the number of strand breaks per plasmid found during illumination with simulated sunlight at a total intensity between 290 and 400 nm of 6 mWatts/cm². Light alone inflicted significant damage (circles). With anatase titanium dioxide the damage was so severe that it could not be accurately quantified. With rutile titanium dioxide the damage was less (squares), but still severe enough to run off the scale at early times. The presence of manganese reduced this damage considerably. Both 0.1% (triangles) and 0.5% (crosses) manganese had very similar effects, reducing the rate of inflicting damage by about 70%, but an increase to 1% (diamonds) had a very beneficial effect, reducing the damage to undetectable levels at the light doses used.

FIG. 8 shows that simulated sunlight alone inflicted significant damage on DNA as revealed by the generation of strand breaks. As the percentage of manganese in the titanium dioxide host lattice was increased the damage in terms of strand breaks decreased. At a manganese content of 1% the damage was almost prevented and was significantly less than the damage inflicted by light alone.

Thus it is believed that such particles may protect DNA from this particular form of damage. The particles may absorb photons of light which would normally inflict damage and divert their energy into non-damaging processes.

The particles may work by photoexcited carrier trapping or by the dopant ions rendering the host lattice p-type. It is believed that these mechanisms may be connected. For particles of less than 20 nm the quantum size effect may also help by shifting the redox potentials.

What is claimed is:

1. A UV screening composition comprising particles having an average primary particle size not exceeding 100 nm which are capable of absorbing UV light so that electrons and positively charged holes are formed within the particles, characterised in that the particles are adapted to minimise migration to the surface of the particles of the electrons and/or the positively charged holes when said particles are exposed to UV light in an aqueous environment said particles being zinc oxide particles incorporating manganese ions or zinc oxide particles incorporating chromium ions, and a carrier.

2. A composition according to claim 1 wherein the chromium or manganese ions are in the 3+ state.

3. A composition according to claim 2 wherein the chromium or manganese ions are present in an amount of from about 0.1 to 1 atom %.

4. A composition according to claim 1 wherein the size of the particles is from 1 to 50 nm.

5. A composition according to claim 1 wherein the particles have an outer coating.

6. A method for preparing a composition as defined in claim 1 which comprises associating the particles with a carrier.

7. A composition according to claim 1 wherein said composition is formulated for cosmetic topical application.

8. A composition according to claim 7 wherein said composition is a sunscreen.

9. A composition according to claim 1 formulated as a paint or coating.

10. The UV screening composition of claim 1, further comprising UVA, UVB or broad-band sunscreen agents.

* * * * *